United States Patent [19]

Liu

[11] 4,429,146

[45] Jan. 31, 1984

[54] SUBSTITUTED DIPHENYL ETHER HERBICIDES AND PROCESS FOR USE

[75] Inventor: Kou-Chang Liu, Wayne, N.J.

[73] Assignee: GAF Corporation, New York, N.Y.

[21] Appl. No.: 368,558

[22] Filed: Apr. 15, 1982

[51] Int. Cl.³ .................................................. C07C 79/46
[52] U.S. Cl. .................................. 560/21; 260/455 R; 260/465 D; 260/507 R; 564/166; 71/107
[58] Field of Search .................. 560/31, 21; 71/107; 260/455 R, 465 D, 507 R

[56] References Cited

FOREIGN PATENT DOCUMENTS 2950401 2/1981 Fed. Rep. of Germany ........ 560/21

Primary Examiner—Paul J. Killos
Attorney, Agent, or Firm—Marilyn J. Maue; J. Gary Mohr; Joshua J. Ward

[57] ABSTRACT

This invention relates to substituted diphenyl ethers having selective herbicidal properties and having the formula:

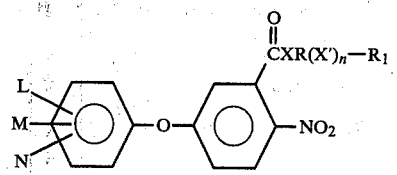

wherein

R is a saturated or unsaturated, straight chain or branched aliphatic hydrocarbon radical of from 1 to 18 carbon atoms wherein one or more of the —CH$_2$— groups can be replaced with —O—, —S—, —S—S—, —SO—, —SO$_2$— or —NR$_2$— and said hydrocarbon radical is optionally substituted with halogen, trihalomethyl, cyano, aryl, hydroxy, alkoxy, nitro or cycloalkyl having 3 to 6 carbon atoms;

R$_1$ is

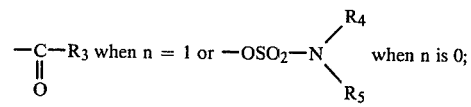

R$_3$ is

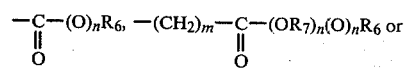

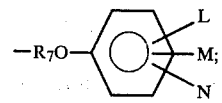

R$_2$ is hydrogen or a saturated or unsaturated straight or branched chain aliphatic radical having from 1 to 8 carbon atoms, optionally substituted with halogen, hydroxy, alkoxy, cyano or nitro;

R$_4$ and R$_5$ are independently a saturated or unsaturated, straight or branched chain aliphatic radical having 1 to 8 carbon atoms optionally substituted with halogen, trihalomethyl, alkoxy or cyano; hydrogen or phenyl optionally substituted with halogen, alkyl, alkoxy, trihalomethyl, nitro or cyano;

R$_6$ is a saturated or unsaturated straight chain or branched aliphatic radical containing from 1 to 8 carbon atoms, optionally substituted with halogen, trihalomethyl, cyano, hydroxy, nitro, acetoxy, alkoxy, thioalkoxy or aryl; an aryl radical optionally substituted with halogen, trihalomethyl, hydroxy, cyano, nitro, alkyl or alkoxy; a cyclic 3–6 membered ring alkylene or 5–6 membered ring alkenylene or benzyl optionally substituted with halogen, trihalomethyl, alkyl, hydroxy, alkoxy or cyano;

R$_7$ is an alkylene diradical having from 1 to 6 carbon atoms;

X and X' are each independently —O—, —S— or —NR$_2$—

L, M and N are each independently hydrogen, hydroxy, halogen, trihalomethyl, nitro, cyano, alkyl or alkoxy having from 1 to 4 carbon atoms and

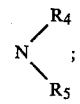

m has a value of from 1 to 6 and
n in each instance has a value of from 0 to 1.

21 Claims, No Drawings

SUBSTITUTED DIPHENYL ETHER HERBICIDES AND PROCESS FOR USE

BACKGROUND OF THE INVENTION

1. Field of the Invention

This invention relates to novel compounds which are selective herbicides of high activity.

2. Description of the Prior Art

Certain phenoxybenzoates show herbicidal activity and are disclosed in e.g. U.S. Pat. Nos. 3,652,645; 3,784,635; 3,798,276; 3,928,416; 3,941,830; 3,979,437; 4,001,005; 4,002,662; 4,046,798; 4,063,929; 4,164,408; 4,164,409; 4,164,410; 4,178,169 and 4,185,995. However, the herbicidal effectiveness and selectivity of a given phenoxybenzoate cannot be predicted from an examination of its chemical structure. Often quite closely related compounds will have significantly different weed control capabilities and crop selectivity.

SUMMARY OF THE INVENTION

In accordance with the present invention, there is provided novel herbicidal diphenyl ethers having the formula:

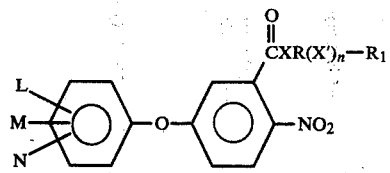

wherein

R is a saturated or unsaturated, straight chain or branched aliphatic hydrocarbon radical of from 1 to 18 carbon atoms wherein one or more of the —CH$_2$— groups can be replaced with —O—, —S—, —S—S—, —SO—, —SO$_2$— or —NR$_2$— and said hydrocarbon radical is optionally substituted with halogen, trihalomethyl, cyano, aryl, hydroxy, alkoxy, nitro or cycloalkyl having 3 to 6 carbon atoms;

R$_1$ is

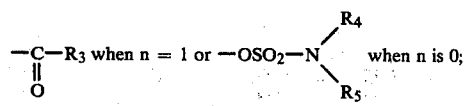

R$_3$ is

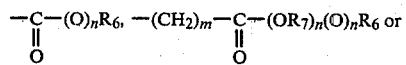

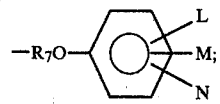

R$_2$ is hydrogen or a saturated or unsaturated straight or branched chain aliphatic radical having from 1 to 8 carbon atoms, optionally substituted with halogen, hydroxy, alkoxy, cyano or nitro;

R$_4$ and R$_5$ are independently a saturated or unsaturated, straight or branched chain aliphatic radical having 1 to 8 carbon atoms optionally substituted with halogen, trihalomethyl, alkoxy or cyano; hydrogen or phenyl optionally substituted with halogen, alkyl, alkoxy, trihalomethyl, nitro or cyano;

R$_6$ is a saturated or unsaturated straight chain or branched aliphatic radical containing from 1 to 8 carbon atoms, optionally substituted with halogen, trihalomethyl, cyano, hydroxy, nitro, acetoxy, alkoxy, thioalkoxy or aryl; an aryl radical optionally substituted with halogen, trihalomethyl, hydroxy, cyano, nitro, alkyl or alkoxy; a cyclic 3–6 membered ring alkylene or 5–6 membered ring alkenylene or benzyl optionally substituted with halogen, trihalomethyl, alkyl, hydroxy, alkoxy or cyano;

R$_7$ is an alkylene diradical having from 1 to 6 carbon atoms;

X and X' are each independently —O—, —S— or —NR$_2$—

L, M and N are each independently hydrogen, hydroxy, halogen, trihalomethyl, nitro, cyano, alkyl or alkoxy having from 1 to 4 carbon atoms and

m has a value of from 1 to 6 and n in each instance has a value of from 0 to 1.

Of the above compounds, those wherein L, M and N are chlorine, trifluoromethyl and hydrogen respectively and wherein R is a lower alkylene diradical or an oxyalkylene diradical; X and X' are oxygen or sulfur are preferred.

The novel compounds of the invention have been found to show excellent activity as weed control agents towards crops of major agricultural importance.

Representative examples of the compounds of this invention, embraced within the formula are given in following Table I.

TABLE I
REPRESENTATIVE HERBICIDES

Structure:

L,M,N-substituted phenyl—O—phenyl(NO₂)—C(=O)—CXRX'—C(=O)—R₃

| Compound | L | M | N | X | X' | R | R₃ |
|---|---|---|---|---|---|---|---|
| 2-(2,4-Dichlorophenoxyacetoxy)ethyl 5-(2-chloro-4-trifluoromethylphenoxy)-2-nitrobenzoate | 2-Cl | 4-CF₃ | H | O | O | —CH₂CH₂— | —CH₂—(2,4-diCl-C₆H₃-O) |
| 8-(2,4-Dichlorophenoxyacetoxy)-3,5-dioxaoctyl 5-(2-chloro-4-trifluoromethylphenoxy)-2-nitrobenzoate | 2-Cl | 4-CF₃ | H | O | O | —(CH₂CH₂O)₂—CH₂CH₂— | —CH₂—(2,4-diCl-C₆H₃-O) |
| 2-(Methyloxalyloxy)ethyl 5-(2-chloro-4-trifluoromethylphenoxy)-2-nitrobenzoate | 2-Cl | 4-CF₃ | H | O | O | —CH₂—CH₂— | —C(=O)—OCH₃ |
| 2-(Ethyloxalyloxy)ethyl 5-(2-chloro-4-trifluoromethylphenoxy)-2-nitrobenzoate | 2-Cl | 4-CF₃ | H | O | O | —CH₂—CH₂— | —COCH₂CH₃ |
| 2-[2-(Methoxycarbonyl)propionyloxy]ethyl 5-(2-chloro-4-trifluoromethylphenoxy)-2-nitrobenzoate | 2-Cl | 4-CF₃ | H | O | O | —CH₂CH₂— | —CH₂CH₂—C(=O)—OCH₃ |
| 2-[(2-Cyano-4-nitrophenoxy)propionyloxy]ethyl 5-(2-chloro-4-trifluoromethylphenoxy)-2-nitrobenzoate | 2-Cl | 4-CF₃ | H | O | O | —CH₂CH₂— | —CH₂—(2-CN-4-NO₂-C₆H₃-O) |
| 2-(2,4,6-Trichlorophenoxyacetamido)ethyl 5-(2-chloro-4-trifluoromethylphenoxy)-2-nitrobenzamide | 2-Cl | 4-CF₃ | H | NH | NH | —CH₂CH₂— | —CH₂—(2,4,6-triCl-C₆H₂-O) |
| 2-(Pyruvyl)ethyl 5-(2-chloro-4-trifluoromethylphenoxy)-2-nitrobenzoate | 2-Cl | 4-CF₃ | H | O | O | —CH₂CH₂— | —C(=O)—CH₃ |

TABLE I-continued
REPRESENTATIVE HERBICIDES

| Name | | | | | | |
|---|---|---|---|---|---|---|
| 2-[2-(Ethoxycarbonyl)propionyloxy]ethyl 5-(2-chloro-4-trifluoromethylphenoxy)-2-nitrobenzoate | 2-Cl | 4-CF$_3$ | H | O | —CH$_2$CH$_2$— | —CH$_2$CH$_2$—C(=O)—O—CH$_2$CH$_3$ |
| 2-[3-[(2-Methoxyethoxy)carbonyl]butynyloxy]ethyl 5-(2-chloro-4-trifluoromethylphenoxy)-2-nitrobenzoate | 2-Cl | 4-CF$_3$ | H | O | —CH$_2$CH$_2$— | —(CH$_2$)$_3$—C(=O)—O(CH$_2$)$_2$OCH$_3$ |
| 2-[3-[(7-Chloro-3,6-dioxapentyloxy)carbonyl]butynyloxy]ethyl 5-(2-chloro-4-trifluoromethylphenoxy)-2-nitrobenzoate | 2-Cl | 4-CF$_3$ | H | O | —(CH$_2$)$_3$— | —(CH$_2$)$_3$—C(=O)—(OCH$_2$CH$_2$)$_2$CH$_2$Cl |
| 5-(Methoxycarbonylacetoxy)-3-oxapentyl 5-(2-chloro-4-trifluoromethylphenoxy)-2-nitrobenzoate | 2-Cl | 4-CF$_3$ | H | O | —CH$_2$CH$_2$—O—CH$_2$CH$_2$— | —CH$_2$—C(=O)—CH$_3$ |
| 2-[2-(Chloromethoxycarbonyl)propionyloxy]ethyl 5-(2-chloro-4-trifluoromethylphenoxy)-2-nitrobenzoate | 2-Cl | 4-CF$_3$ | H | O | —CH$_2$CH$_2$— | —CH$_2$CH$_2$—C(=O)—O—CH$_2$Cl |
| 2-[2-(Ethoxyethoxycarbonyl)propionyloxy]ethyl 5-(2-chloro-4-trifluoromethylphenoxy)-2-nitrobenzoate | 2-Cl | 4-CF$_3$ | H | O | —CH$_2$CH$_2$— | —CH$_2$CH$_2$—C(=O)—OCH$_2$CH$_2$OCH$_2$CH$_3$ |
| 4-(2-Chlorophenoxycarbonyl)butyryloxy 5-(2-chloro-4-trifluoromethylphenoxy)-2-nitrobenzoate | 2-Cl | 4-CF$_3$ | H | O | —CH$_2$CH$_2$— | —CH$_2$CH$_2$—C(=O)—O—(2-Cl-C$_6$H$_4$) |
| 5-[2-(Ethoxycarbonyl)propionyloxy]-3-thiapentyl 5-(2-chloro-4-trifluoromethylphenoxy)-2-nitrobenzoate | 2-Cl | 4-CF$_3$ | H | O | —CH$_2$CH$_2$—S—CH$_2$CH$_2$— | —CH$_2$CH$_2$—C(=O)—CH$_3$ |
| 2-[(Methoxycarbonyl)propylthio]ethyl 5-(2-chloro-4-trifluoromethylphenoxy)-2-nitrobenzoate | 2-Cl | 4-CF$_3$ | H | S | —CH$_2$CH$_2$— | —CH$_2$CH$_2$—CO—CH$_3$ |
| 5-(Ethyloxalyloxy)-3-oxapentyl 5-(2-chloro-4-trifluoromethylphenoxy)-2-nitrobenzoate | 2-Cl | 4-CF$_3$ | H | O | —CH$_2$CH$_2$OCH$_2$CH$_2$— | —C(=O)—OCH$_2$CH$_3$ |
| 2-(chloropyruvyl)ethyl 5-(2-chloro-4-trifluoromethylphenoxy)-2-nitrobenzoate | 2-Cl | 4-CF$_3$ | H | O | —CH$_2$CH$_2$— | —C(=O)—CH$_2$Cl |

TABLE I-continued
REPRESENTATIVE HERBICIDES

| Name | Col1 | Col2 | Col3 | Col4 | Col5 |
|---|---|---|---|---|---|
| 5-methyloxyalyloxy-3-oxapentyl 5-(2-chloro-4-trifluoromethylphenoxy)-2-nitrobenzoate | 2-Cl | 4-CF$_3$ | H | O | —CH$_2$CH$_2$O—CH$_2$CH$_2$— | —C(=O)—OCH$_3$ |
| 8-(pyruvyl)-3,6-dioxaoctyl-5-(2,4,6-trichlorophenoxy)-2-nitrobenzoate | 2-Cl | 4-Cl | 6-Cl | O | —CH$_2$CH$_2$(OCH$_2$CH$_2$)$_2$— | —C(=O)—CH$_3$ |
| 2-(methyloxalyloxy)ethyl-5-[2,4-di-(trifluoromethylphenoxy)]-2-nitrobenzoate | 2-CF$_3$ | 4-CF$_3$ | H | O | —CH$_2$CH$_2$— | —C(=O)—OCH$_3$ |
| 4-(methyloxalyloxy)butyl-5-(2-chloro-4-trifluoromethylphenoxy)-2-nitrobenzoate | 2-Cl | 4-CF$_3$ | H | O | —CH$_2$CH$_2$CH$_2$CH$_2$— | —C(=O)—OCH$_3$ |
| 2-chlorophenyl oxalyloxy)ethyl 5-(2,6-dimethyl-4-nitrophenoxy)-2-nitrobenzoate | 2-CH$_3$ | 4-NO$_2$ | 6-CH$_3$ | O | —CH$_2$CH$_2$— | —C(=O)—O—(2-chlorophenyl) |
| 2-(2,4-dichlorophenoxyacetoxy)ethyl 5-(2-chloro-4-trifluoromethylphenoxy)-2-nitrobenzoate | 2-Cl | 4-CF$_3$ | H | O | —CH$_2$CH$_2$— | —CH$_2$—O—(2,4-dichlorophenyl) |
| 8-(2,4-dichlorophenoxyacetoxy)-3,6-dioxaoctyl 5-(2-chloro-4-trifluoromethylphenoxy)-2-nitrobenzoate | 2-Cl | 4-CF$_3$ | H | O | —(CH$_2$CH$_2$O)$_2$CH$_2$CH$_2$— | —CH$_2$—O—(2,4-dichlorophenyl) |
| 5-(2-chlorophenoxyacetoxy)-3-thiopentyl 5-(2-chloro-4-trifluoromethylphenoxy)-2-nitrobenzoate | 2-Cl | 4-CF$_3$ | H | O | —CH$_2$CH$_2$—S—CH$_2$CH$_2$— | —CH$_2$—O—(2-chlorophenyl) |
| 2-[2-(2,4-dichlorophenoxy)propionyloxy)ethyl 5-(2-chloro-4-trifluoromethylphenoxy)-2-nitrobenzoate | 2-Cl | 4-CF$_3$ | H | O | —CH$_2$CH$_2$— | —CH$_2$CH$_2$—O—(2,4-dichlorophenyl) |
| 2-(2,4-dinitrophenoxyacetoxy)ethyl 5-(2-chloro-4-trifluoromethylphenoxy)-2-nitrobenzoate | 2-Cl | 4-CF$_3$ | H | O | —CH$_2$CH$_2$— | —CH$_2$—O—(2,4-dinitrophenyl) |

TABLE I-continued
REPRESENTATIVE HERBICIDES

| Compound | L | M | N | O | R | |
|---|---|---|---|---|---|---|
| 2-(2-methylphenoxyacetoxy)ethyl 5-(2,4,6-trichlorophenoxy)-2-nitrobenzoate | 2-Cl | 4-Cl | 6-Cl | O | —CH₂CH₂— | —CH₂—O—(2-methylphenyl) |
| 2-(4-hydroxyphenoxyacetoxy)ethyl 5-(2-cyano-4-trifluoromethylphenoxy)-2-nitrobenzoate | 2-CN | 4-CF₃ | H | O | —CH₂CH₂— | —CH₂—O—(4-hydroxyphenyl) |
| 4-(2,4-dichlorophenoxyacetoxy)-2-buten-1-yl 5-(2,4-dinitrophenoxy)-2-benzoate | 2-NO₂ | 4-NO₂ | H | O | —CH₂CH=CHCH₂— | —CH₂—O—(2,4-dichlorophenyl) |
| 2-(2,4-dichlorophenoxyacetoxy)ethyl 5-(2-chloro-4-trifluoromethylphenoxy)-2-nitrobenzoate | 2-Cl | 4-CF₃ | H | O | —CH₂CH₂— | —CH₂—O—(2,4-dichlorophenyl) |
| 2-(Chloromethyloxalyloxy)ethyl 5-(2-chloro-4-trifluoromethylphenoxy)-2-nitrobenzoate | 2-Cl | 4-CF₃ | H | O | —CH₂CH₂— | —COCH₂Cl (C=O) |
| 6-(2,4-Dichlorophenoxyacetoxy) 3,4-dithiahexyl 5-(2-chloro-4-trifluoromethylphenoxy)-2-chlorobenzoate | 2-Cl | 4-CF₃ | H | O | —CH₂—CH₂—S—S—CH₂CH₂— | —CH₂O—(2,4-dichlorophenyl) |

General structure:

$$\text{L, M, N substituted phenyl—O—phenyl(NO}_2\text{)—C(=O)—O—R—O—S(=O)}_2\text{—N(R}_4\text{)(R}_5\text{)}$$

| Compound | L | M | N | R | R₄ | R₅ |
|---|---|---|---|---|---|---|
| 2-(N,N—Dimethylsulfamoyloxy)ethyl 5-(2-chloro-4-trifluoromethylphenoxy)-2-nitrobenzoate | 2-Cl | 4-CF₃ | H | —CH₂CH₂— | —CH₃ | —CH₃ |
| 5-(N,N—Diethylsulfamoyloxy)-3-oxapentyl 5-(2-chloro-4-trifluoromethylphenoxy)-2-nitrobenzoate | 2-Cl | 4-CF₃ | H | —CH₂CH₂OCH₂CH₂— | —CH₂CH₃ | —CH₂CH₃ |
| 5-(N,N—Diethylsulfamoyloxy)-3-thiapentyl 5-(2-chloro-4-trifluoromethylphenoxy)-2-nitrobenzoate | 2-Cl | 4-CF₃ | H | —CH₂CH₂—S—CH₂CH₂— | —CH₂CH₃ | —CH₂CH₃ |

TABLE I-continued

REPRESENTATIVE HERBICIDES

| Name | | | | |
|---|---|---|---|---|
| 2-(N,N—Dimethylsulfamoyloxy)ethyl 5-(2,4,6-trichlorophenoxy)-2-nitrobenzoate | 2-Cl | 4-Cl | 2-Cl | —CH₂—CH₂— | —CH₃ | —CH₃ |
| 8-[N—(3-Chlorophenyl)sulfamoyl]3,5-dioxaoctyl 5-(2-chloro-4-trifluoromethylphenoxy)-2-nitrobenzoate | 2-Cl | 4-CF₃ | H | —CH₂CH₂OCH₂CH₂OCH₂CH₂— | H | (4-chlorophenyl) |
| 3-[N—(2-Naphthyl)sulfamoyl]propyl 5-(2-chloro-4-trifluoromethylphenoxy)-2-nitrobenzoate | 2-Cl | 4-CF₃ | H | —CH₂CH₂CH₂— | H | (2-naphthyl) |
| 2-(N,N—Dipropylsulfamoyloxy)ethyl 5-(2-chloro-4-trifluoromethylphenoxy)-2-nitrobenzoate | 2-CF₃ | 4-CF₃ | H | —CH₂CH₂— | —CH₂CH₂CH₃ | —CH₂CH₂Cl |
| 5-(N,N—Diallylsulfamoyloxy)-3-thiadioxo-pentyl 5-(2-chloro-4-trifluoromethylphenoxy)-2-nitrobenzoate | 2-Cl | 4-CF₃ | H | —CH₂CH₂S(=O)(=O)—CH₂CH₂— | —CH₂CH=CH₂ | —CH₂CH=CH₂ |
| 2-(N—isopropylsulfamoyloxy)ethyl 5-(2-chloro-4-trifluoromethylphenoxy)-2-nitrobenzoate | 2-Cl | 4-CF₃ | H | —CH₂CH₂— | H | —CH(CH₃)CH₃ |
| 2-N—(2-chloro-4-cyanophenylsulfamoyloxy)ethyl 5-(2-chloro-4-trifluoromethylphenoxy)-2-nitrobenzoate | 2-Cl | 4-CF₃ | H | —CH₂CH₂— | H | (2-chloro-4-cyanophenyl) |

The compounds of this invention can be prepared by reacting a phenoxynitrobenzoate having the formula:

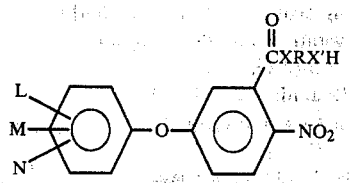

with a carbonyl-containing compound having the formula:

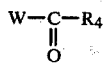

or, when X' is oxygen, an sulfamoyl chloride having the formula

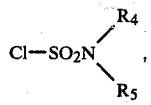

wherein W is hydroxy, chlorine or bromine and L, M, N, X, X', $R_2$, $R_4$ and $R_5$ are as defined above, at a temperature of between about 0° and about 200° C. under from about 1 to about 5 atmospheres pressure for a period of from about 0.5 to about 20 hours; preferably when W is —OH at a temperature of between about 100° and about 160° C. and when W is halogen, at a temperature between about 20° C. and about 80° C., under atmospheric pressure for a period of from about 1 to about 10 hours.

Representative examples of carbonyl-containing compounds include 2,4-dichlorophenoxyacetyl chloride, methyloxalyl chloride, ethyloxalyl chloride, carbomethoxypropionyl chloride, pyruvic acid, carboethoxypropanoyl chloride and the like.

Representative examples of phenoxynitrobenzoate compounds include:

2-Hydroxyethyl-5-(2-chloro-4-trifluoromethylphenoxy)-2-nitrobenzoate
4-Hydroxybutyl{5-[2-chloro-4-(trifluoromethyl)phenoxy]-2-nitro}benzoate
6-Hydroxyhexyl{5-[2-chloro-4-(trifluoromethyl)phenoxy]-2-nitro}benzoate
4-Hydroxy-2-buten-1-yl{5-[2-chloro-4-(trifluoromethyl)phenoxy]-2-nitro}benzoate
2-Hydroxyethyl[5-(2,4-dichlorophenoxy)-2-nitro]benzoate
4-Hydroxybutyl[5-(2,4-dichlorophenoxy)-2-nitro]benzoate
4-Hydroxy-2-buten-1-yl[5-(2,4-dichloro)phenoxy-2-nitro]benzoate
4-Hydroxy-2-butyn-1-yl[5-(2,4-dichlorophenoxy)-2-nitro]benzoate
3-Hydroxypropyl{5-[2-chloro-4-(trifluoromethyl)phenoxy]-2-nitro}benzoate
3-Hydroxy-2,2-dimethylpropyl{5-[2-chloro-4-(trifluoromethyl)phenoxy]-2-nitro}benzoate
4-Hydroxy-2-butyn-1-yl{5-[2-chloro-4-(trifluoromethyl)phenoxy]-2-nitro}benzoate
3-Hydroxy-2-butyl{5-[2-chloro-4-(trifluoromethyl)phenoxy]-2-nitro}benzoate
5-Hydroxypentyl{5-[2-chloro-4-(trifluoromethyl)phenoxy]-2-nitro}benzoate
2-Allyl-3-hydroxypropyl{5-[2-chloro-4-(trifluoromethyl)phenoxy]-2-nitro}benzoate
3-Hydroxy-3-methylbutyl{5-[2-chloro-4-(trifluoromethyl)phenoxy]-2-nitro}benzoate
2-Hydroxypropyl{5-[2-chloro-4-(trifluoromethyl)phenoxy]-2-nitro}benzoate
2-Hydroxyethyl{5-[2-chloro-4-(trifluoromethyl)6-nitro]phenoxy-2-nitro}benzoate
2-Hydroxyethyl{5-[2,4-di(trifluoromethyl)phenoxy]-2-nitro}benzoate
2-Hydroxyethyl[5-(2,4-dichloro-6-methyl)phenoxy-2-nitro]benzoate
2-Hydroxyethyl[5-(2-chloro-4-methoxy)phenoxy-2-nitro]benzoate
2-Hydroxyethyl[5-(2-chloro-4-cyano)phenoxy-2-nitro]benzoate
4-Hydroxy-2-butyn-1-yl[5-(2,4-dichloro)phenoxy-2-nitro]benzoate Suitable sulfamoyl chloride reactants include dimethylsulfamoyl chloride, N-(3-chlorophenyl)-N-methylsulfamoyl chloride, and the like.

The phenoxy nitrobenzoate reactants can be prepared according to the process of copending applications Ser. No. 358,974, filed Mar. 17, 1982 and Ser. No. 239,286, filed Mar. 2, 1981. The mole ratio of said benzoate to carbonyl-containing compound or sulfamoyl chloride can vary between about 1:1 and about 1:10. Although stoichiometric amounts are most desirable for the reaction, excess carbonyl compound or sulfamoyl chloride can serve as a recyclable solvent for the system. While other diluent can be employed if desired such as pyridine, tetrahydrofuran, triethylamine and mixtures thereof, it is to be understood that the reaction can also be carried out in the absence of a diluent. When a solvent is employed, the concentration of the reactant benzoate can vary between about 10 wt.% and about 80 wt.%.

The product of the reaction is recovered by conventional means such as stripping, distillation or precipitation.

The compounds of this invention are useful both as pre-emergent and post-emergent herbicides and are highly selective to crops. Among the crops on which these herbicides may be advantageously employed, are, for example, gramineae including rice, cereal crops, sorghum, corn, wheat and safflower; leguminosae including beans, peas, peanuts, soybeans and lentiles; solanaceae including potato, pepper, tobacco and tomato; curciferae including cabbages and turnips; malvaceae including cotton; umbelliferae including carrots and parsley and Liliaceae including onion, scallion, and shallot. Cheet grass, foxtail, barnyard grass, curled dock, yellow rocket, chickweed, pigweed, lambsquarter, morning glory, Japanese millet, crabgrass, ragweed, cocklebur, velvet leaf, coffee weed, wild mustard and black mustard are among the weed species controlled by the present herbicides. Accordingly, the novel substituted diphenyl ethers of this invention are broad spectrum herbicides.

The herbicides of this invention may be applied in any amount which will give the required control of weeds depending on the type of weed and degree of infestation. A preferred rate of application of the benzoates is from 0.05 to 8 lbs. per acre. In practical application, the compounds may be applied in solid, liquid or in vaporized form, or, as it is generally done, as an active ingredient in a standard herbicidal composition or formulation which comprises a carrier. A generally accepted carrier is a substance which can be used to dissolve, disperse or diffuse the herbicidal components in the composition. Non-limiting examples of liquid carriers include water, organic solvents such as alcohols, ketones, halogenated hydrocarbons, aromatic hydrocarbons, ethers, amides, esters, nitriles, mineral oils, palm oil and the like. Non-limiting examples of solid carriers include Kaolin, bentonite, talc, diatomaceous earth, vermiculite, clay, gypsum, grain and seed hulls, ground corn cobs and the like. In addition to a carrier, it is usually desirable to add to the herbicidal formulation additives such as emulsifying agents, wetting agents, binding agents, stabilizer and the like or thickeners as desired for particular weather conditions or applications. The compounds may be formulated, for example, as a dust, wettable powders, paste, emulsifiable concentrates, granular formulations or as liquids or aerosols.

The phenoxybenzoates of this invention may be applied along with plant growth regulators, insecticides, fungicides, nematocides and fertilizers. They may be applied in combination with one or more other herbicides. Non-limiting examples of other herbicides which can be incorporated with the phenoxybenzoates of this invention are anilides, such as N-methoxymethyl(2,6-diethylphenyl)chloroacetamide; dinitroanilines, such as $\alpha,\alpha,\alpha$-trifluoro-2,6-dinitro-N,N-di-propyl-p-toluidine; carboxylic acids and derivatives; triazines; substituted urea; carbamates; thiocarbamates; uracils; heterocycles and organo phosphorous compounds.

Reference is now had to the following examples which illustrate preferred embodiments of the invention set forth herein. It is to be understood, however, that these examples should not be construed as limiting to the scope of the invention as more broadly defined herein above and in the following claims.

EXAMPLE 1

Preparation of 2-(2,4-Dichlorophenoxyacetoxy)ethyl 5-(2-chloro-4-trifluoromethylphenoxy)-2-nitrobenzoate (A) 5-(2-Chloro-4-trifluoromethylphenoxy)benzoic acid.

m-Hydroxybenzoic acid (828.4 g, 6.0 mole) was added to a solution of potassium hydroxide (840 g, 12.7 mole) and DMSO (2500 g). 3,4-Dichlorobenzotrifluoride (1000 ml) was added after distilling off 200 ml of DMSO and water. The resultant mixture was heated at 140°-150° C. for 54 hrs. The solvent was then removed under reduced pressure and the remaining brownish slurry was poured into an ice water mixture (8 liters). The aqueous solution was extracted with methylene chloride and the yellowish product was precipitated out at pH 2 with conc. HCl (400 ml) filtration, washing with water and recrystallization from toluene (3000 ml) and MeOH (400 ml) afforded 1148.7 g of the desired product; m.p. 111°-118° C.

(B) 5-(2-Chloro-4-trifluoromethylphenoxy)-2-nitrobenzoic acid.

3-(2-Chloro-4-trifluoromethylphenoxy)benzoic acid (275.9 g, 0.935 mole), acetic anhydride (276 g, 2.7 mole), glacial acetic acid (276 g, 4.6 mole) and conc. $H_2SO_4$ (44 g) were charged into a three-neck 5 liter flask equipped with a mechanical stirrer, thermometer and an addition funnel. Nitric acid (90%, 91.7 g, 1.3 mole) was added at 15°-25° C. over 0.5 hr. The cooling bath was substituted with a water bath and the reaction was stirred for 1.5 hrs. at 30° C. The reaction was quenched with 1250 ml of water (at 30° C.), stirred for 0.25 hr. The resultant yellow precipitate was filtered and washed with 2 liters of water. Recrystallization from toluene (750 ml) afforded 271.6 g of 5-(2-chloro-4-trifluoromethylphenoxy)-2-nitrobenzoic acid; m.p. 120°-121° C.

(C) 5-[2-Chloro-4-trifluoromethylphenoxy]-2-nitrobenzoyl chloride.

A solution of 5-[2-chloro-4-trifluoromethylphenoxy]-2-nitrobenzoic acid (448.1 g, 1.24 mole), thionyl chloride (458 g) and toluene (250 ml) was held at reflux for 8 hrs. The excess thionyl chloride and the solvent were stripped off under reduced pressure to give a reddish solid, which upon recrystallization from hexane-toluene afforded 282.9 g of the desired benzoyl chloride as a light yellow crystalline solid; m.p. 63°-69° C.

(D) 2-Hydroxyethyl 5-(2-chloro-4-trifluoromethylphenoxy)-2-nitrobenzoate.

A well-stirred solution of 5-[2-chloro-4-(trifluoromethyl)phenoxy]benzoyl chloride (282.9 g, 0.74 mole) and ethylene glycol (1000 ml) was heated at 145° C. for 3 hours. Then triethylamine (30 ml) was added. The solution was reheated at 142° C. for 8 hours. After most of the ethylene glycol was distilled off under reduced pressure, the oil was taken up in 1700 ml of methylene chloride. The methylene chloride solution was washed three times with water, dried over $MgSO_4$ and concentrated to a gummy material. Molecular distillation afforded 226.2 g (75% yield) of a pale yellow gum which solidified on standing. 3.5 g of the solid was recrystallized from hexane-toluene to give 2.8 g of white solid; m.p. 75°-78° C.; nmr ($CDCl_3$) $\delta 0.3.32$ (S, 1H), 3.67-4.12 (m, 2H), 4.15-4.63 (m, 2H), 7.02-8.25 (m, 6H); ir ($CHCl_3$) 1749 $Cm^{-1}$.

(E) 2,4-Dichlorophenoxyacetyl chloride.

A mixture of 2,4-dichlorophenoxyacetic acid (38 g) and thionyl chloride (100 ml) was held at reflux for 2 hrs. The excess thionyl chloride was removed from the resulting clear solution under reduced pressure to yield 43.7 g pale yellow oil; nmr ($CDCl_3$) $\delta 4.95$ (S, 2H), 6.68-7.42 (m, 3H).

(F) 2,4-Dichlorophenoxyacetyl chloride (5.3 g, 0.25 mole), was added portionwise to a solution of 2-hydroxyethyl 5-(2-chloro-4-trifluoromethylphenoxy)-2-nitrobenzoate (10 g, 0.25 mole) and pyridine (70 ml). The resulting mixture was heated to 60° C. for 1 hr., cooled and taken into 500 ml $CH_2Cl_2$. The methylene chloride solution was washed two times with water, dried and concentrated to 12.5 g of gummy material. The crude gum was chromatographed through silica gel (3:10, ethyl acetate:hexane) to give 2.3 g of pure 2-(2,4-dichlorophenoxyacetoxy)ethyl 5-(2-chloro-4-trifluoromethylphenoxy)-2-nitrobenzoate; nmr (DMSO) 4.20-4.76 (m, 4H), 5.04 (S, 2H), 6.96-8.42 (m, 9H); ir ($CHCl_3$) 1755, 1770 $Cm^{-1}$.

Other compounds of this type are also prepared according to this example by proper substitution of the 2,4-dichlorophenoxyacetyl chloride reactant. For instance, 2-[(2-cyano-4-nitrophenoxy)-propionyloxy]ethyl 5-(2-chloro-4-trifluoromethylphenoxy)-2-nitrobenzoate is prepared by substituting 2-[(2-cyano-4-nitrophenoxy)propionyl]chloride; 2-(2,4,6-trichlorophenoxyacetoxy)ethyl 5-(2-chloro-4-trifluoromethylphenoxy)-2-nitrobenzoate is prepared by substituting 2-(2,4,6-trichlorophenoxyacetyl chloride; etc.

EXAMPLE 2

Preparation of 8-(2,4-Dichlorophenoxyacetoxy)-3,6-dioxaoctyl 5-(2-chloro-4-trifluoromethylphenoxy)-2-nitrobenzoate (A) 8-Hydroxy-3,6-dioxaoctyl 2,4-dichlorophenoxyacetate 2,4-Dichlorophenoxyacetyl chloride (40.0 g, 0.18 mole) was added dropwise to a solution of trimethylene glycol (32 g, 0.21 mole) and triethylamine (21 g) over 1 hr. A salt precipitated out and stirring became difficult. Another 10 ml of trimethylene glycol and 50 ml of THF was added. The mixture was held at reflux for 3 hrs. After the solvent was stripped off, the residue was taken into 650 ml of ether, washed two times with NaHCO$_3$ solution and two times with water. The ether solution afforded 40.6 g of brownish gum. A sample of 20 g of the gum was run through a silica gel column with 10% to 60% ethyl acetate and 90% to 40% hexane as eluent to yeild 5.3 g of pure 8-hydroxy-3,6-dioxaoctyl 2,4-dichlorophenoxyacetate as a yellowish oil; nmr (CDCl$_3$) 2.73 (S, 1H), 3.34 (m, 10H), 4.18–4.49 (m, 2H), 4.73 (S, 2H), 6.62–7.48 (m, 3H); ir (CHCl$_3$) 1750, 1770, 3500, 3620 Cm$^{-1}$.

(B) 5-(2-Chloro-4-trifluoromethylphenoxy)-2-nitrobenzoyl chloride (4.0 g, 0.0105 mole) was added portionwise to a solution of 8-hydroxy-3,6-dioxaoctyl 2,4-dichlorophenoxyacetate (3.5 g, 0.103 mole), triethylamine (1.2 g, 0.103 mole) and THF (40 ml) over 5 mins. The resulting solution was held at reflux for 3 hrs. After the solvent was stripped off, the residue was taken into 2600 ml of ether, washed two times with NaHCO$_3$ solution and two times with water. The ether solution was then dried over MgSO$_4$ and concentrated to 5.9 g of 8-(2,4-dichlorophenoxyacetoxy)-3,6-dioxaoctyl 5-(2-chloro-4-trifluoromethylphenoxy)-2-nitrobenzoate, a brownish gum; nmr (CDCl$_3$) δ3.30–4.02 (m, 8H), 4.25–4.62 (m, 4H), 4.70 (S, 2H), 6.65–8.24 (m, 9H); ir (CHCl$_3$) 1750, 1770 Cm$^{-1}$.

EXAMPLE 3

Preparation of 2-(Methyloxalyloxy)ethyl 5-(2-chloro-4-trifluoromethylphenoxy)-2-nitrobenzoate Methyloxalyl chloride (2.3 g, 0.0 188 mole) was added dropwise to a solution of 2-hydroxyethyl 5-(2-chloro-4-trifluoromethylphenoxy)-2-nitrobenzoate (5 g, 0.123 mole), 20 ml of THF (tetrahydrofuran) and triethylamine (1.5 g, 0.127 mole) in 10 minutes. The temperature of reaction solution rose from 23° C. to 40° C. The resulting light yellow solution with white precipitate was heated and held at reflux for 1 hour. The solvent was stripped off and the residue was taken into 400 ml of ether. The ethereal solution was washed two times with NaHCO$_3$ solution and two times with water, dried over MgSO$_4$ and concentrated to 5.7 g of the desired product as a clear yellow gum, nmr (CDCl$_3$) δ3.88 (S, 3H), 4.60 (S, 4H), 6.96–8.22 (m, 6H); ir (CHCl$_3$) 1757, 1782 Cm$^{-1}$.

Other compounds of this type are also prepared according to this example by proper substitution of the methyloxalyl chloride reactant. For instance, 2-(2-chlorophenyloxalyloxy)-ethyl 5-(2-chloro-4-trifluoromethylphenoxy)-2-nitrobenzoate is prepared by substituting 2-(2-chlorophenyl)oxalyl chloride; 2-(chloromethyloxalyloxy)ethyl 5-(2-chloro-4-trifluoromethylphenoxy)-2-nitrobenzoate is prepared by substituting 2-(chloromethyl)oxalyl chloride; etc.

EXAMPLE 4

Preparation of 2-(ethyloxalyloxy)ethyl 5-(2-chloro-4-trifluoromethylphenoxy)-2-nitrobenzoate Ethyloxalyl chloride (2.3 g, 0.0 188 mole) was added dropwise to a solution of 2-hydroxyethyl 5-(2-chloro-4-trifluoromethylphenoxy)-2-nitrobenzoate (5 g, 0.123 mole), 20 ml of THF and triethylamine (1.5 g, 0.127 mole) in 10 minutes. The temperature of reaction solution rose from 23° C. to 40° C. The resulting light yellow solution with white precipitate was heated and held at reflux for 1 hour. The solvent was stripped off and the residue was taken into 400 ml of ether. The ethereal solution was washed two times with NaHCO$_3$ solution and two times with water, dried over MgSO$_4$ and concentrated to 5.7 g of the desired product as a clear yellow gum, (CDCl$_3$) δ1.37 (t, 3H), 4.40 (q, 2H), 4.63 (S, 1H), 6.98–8.28 (m, 6H); ir (CHCl$_3$) 1750, 1770 Cm$^{-1}$.

EXAMPLE 5

Preparation of 2-[2-(Methoxycarbonyl)propionyloxy]ethyl 5-(2-chloro-4-trifluoromethylphenoxy)-2-nitrobenzoate Carbomethoxypropionyl chloride (2.8 g, 0.0186 mole) was added dropwise to a solution of 2-hydroxymethyl 5-(2-chloro-4-trifluoromethylphenoxy)-2-nitrobenzoate (5 g, 0.0123 mole), THF (20 ml) and triethylamine (1.5 g, 0.0127 mole) over 30 minutes. The temperature rose from 23° to 45° C. and yellow solid precipitated out. The mixture was then heated to reflux for 0.5 hours, cooled and concentrated under reduced pressure. The residue was taken into 400 ml of ether and 200 ml of saturated NaHCO$_3$ solution. After being washed two times with water dried over MgSO$_4$, 6.3 g of the product, a clear yellow oil was obtained. The oil is the desired benzoate; nmr (CDCl$_3$) δ2.63 (S, 4H), 3.68 (S, 3H), 4.27–4.72 (m, 4H), 6.96–8.20 (m, 6H); ir (CHCl$_3$) 1745 Cm$^{-1}$ (broad).

Other compounds of this type are also prepared according to this example by proper substitution of the carbomethoxypropionyl chloride reactant. For instance, 2-[2-(chloromethoxycarbonyl)propionyloxyethyl]5-(2-chloro-4-trifluoromethylphenoxy)-2-nitrobenzoate is prepared by substituting carbochloromethoxypropionyl chloride; 2-[2-(ethoxycarbonyl)propionyloxy]ethyl 5-(2-chloro-4-trifluoromethylphenoxy)-2-nitrobenzoate is prepared by substituting carboethoxypropionyl chloride; etc.

EXAMPLE 6

Preparation of 2-(N,N-dimethylsulfamoyloxy)ethyl 5-(2-chloro-4-trifluoromethylphenoxy)-2-nitrobenzoate Dimethylsulfamoyl chloride (7.2 g, 0.05 mole) was added dropwise to a solution of 2-hydroxyethyl 5-(2-chloro-4-trifluoromethylphenoxy)-2-nitrobenzoate (10 g, 0.025 mole), triethylamine (10 ml) and ethyl ether (200 ml). The mixture was heated to and held at reflux for 5 hrs., cooled, added 200 ml of ether and washed three times with water. The ethereal solution was dried over MgSO$_4$, concentrated to 13.9 g of yellow gum. The gummy material was run through a silica gel with 30% acetone-70% cyclohexane as eluent to afford 3.0 g of pure 2-(N,N-dimethylsulfamoyloxy)ethyl 5-(2-chloro-4-trifluoromethylphenoxy)-2-nitrobenzoate as colorless gum; nmr (CDCl$_3$) 2.96 (S, 6H), 3.84 (m, 2H), 4.52 (m, 2H), 6.88–8.24 (m, 6H).

Other compounds of this type are also prepared according to this example by proper substitution of the dimethylsulfamoyl chloride reactant. For instance 2-(N,N-diethylsulfamoyloxy)ethyl 5-(2-chloro-4-trifluoromethylphenoxy)-2-nitrobenzoate is prepared by substituting diethylsulfamoyl chloride; [N-(3-chlorophenyl)-N-methylsulfamoyloxy]ethyl 5-(2-chloro-4-trifluoromethylphenoxy)-2-nitrobenzoate; is prepared by substituting N-(3-chlorophenyl)-N-methyl sulfamoyl chloride; etc.

HERBICIDAL TESTS

The present compounds were tested for herbicidal activity and the results of these tests are reported as follows.

EXAMPLE 7

Tests were made on two flats seeded with species of representative monocotyledonous and dicotyledonous plants. The test chemical was applied to one such flat immediately after it was seeded. The other flat contained plants on which the first true leaves had developed before the chemical was applied. The response was rated 12 to 21 days after treatment on a scale of 0 to 9 where 0 represents no injury and 9 represents complete kill.

The following results are reported in Tables II and III.

TABLE II

Herbicidal Effectiveness of Post-Emergence Application (at 10 lbs./acre)

| Compound of Example No. | MNGTY | MSTD | FOX | JPN | CRB | PIG |
|---|---|---|---|---|---|---|
| 1 | $4^S$ | $5^S$ | $7^N$ | $6^{N,S}$ | $4^N$ | $8^N$ |
| 3 | 9 | 9 | 9 | $8^{S+}$ | 9 | 9 |
| 4 | 9 | 9 | 9 | 8 | 8 | 9 |
| 5 | 9 | 9 | 9 | $8^{S+}$ | 9 | 9 |
| 6 | 9 | 9 | 9 | 9 | 9 | 9 |

TABLE III

Herbicidal Effectiveness of Pre-Emergence Application

| Compound of Example No. | MNGTY | MSTD | FOX | JPN | CRB | PIG |
|---|---|---|---|---|---|---|
| 1 | $7^{E,N}$ | 9 | 9 | 9 | 9 | 9 |
| 3 | 9 | 9 | 9 | 9 | 9 | 9 |
| 4 | 9 | 9 | 7 | 9 | 9 | 9 |
| 5 | 9 | 9 | 9 | 9 | 9 | 9 |
| 6 | 9 | 9 | 9 | 9 | 9 | 9 |

Activity in Tables II and III is rated on a scale of 0–9, i.e. from no visible effect on foliage or plant emergence to 100% destruction. In the above Tables, $N$ = necrosis; $E$ = epinasty; $S$ = moderate stunting and $S+$ = severe stunting.

EXAMPLE 8

Again, tests were made on two flats seeded with species of representative monocotyledonous and dicotyledonous plants. The test chemical was applied to one such flat immediately after it was seeded. The other flat contained plants on which the first true leaves had developed before the chemical was applied. The response was rated 12 to 21 days after treatment on a scale of 0 to 9 where 0 represents no injury and 9 represents complete kill.

The results are shown in the following Tables IV and V.

TABLE IV

Post Emergence Herbicidal Activity & Crop Tolerance

| | Compd. of Ex. 3 (Dosage in lb./acre) | | | Compd. of Ex. 4 (Dosage in lb./acre) | | | Compd. of Ex. 6 (Dosage in lb./acre) | | |
|---|---|---|---|---|---|---|---|---|---|
| PLANT | 4 | 2 | 1 | 4 | 2 | 1 | 4 | 2 | 1 |
| Morning Glory | 9 | 9 | 9 | 9 | 9 | 9 | 9 | 9 | 9 |
| Mustard | 9 | 9 | $7^S$ | 9 | 9 | 9 | 9 | 9 | $7^{S+}$ |
| Yellow Foxtail | 9 | $5^S$ | 2 | 8 | 8 | $6^S$ | 6 | 6 | 3 |
| Japanese Millet | $7^{S+}$ | 5 | 5 | 8 | $5^S$ | 4 | $6^S$ | 4 | 0 |
| Crabgrass | 9 | 9 | $6^S$ | 9 | $8^S$ | $5^S$ | 9 | 9 | $6^{S+}$ |
| Pigweed | 9 | 9 | 9 | 9 | 9 | 9 | 9 | 9 | 9 |
| Cocklebur | 9 | 9 | $8^{S+}$ | 9 | 8 | $5^S$ | $8^{S+}$ | 9 | $8^{S+}$ |
| Velvet Leaf | 9 | 9 | 9 | 9 | 9 | 9 | 9 | 9 | 9 |
| Hemp Sesbania | 9 | 9 | 9 | 9 | 9 | 9 | 9 | 9 | 9 |
| Lambsquarters | 9 | 9 | 9 | 9 | 9 | 9 | 9 | 9 | 9 |
| Soybean | | 5 | | | 3 | | | 4 | |
| Corn | | 1 | | | 2 | | | 0 | |
| Rice | | 3 | | | 1 | | | 2 | |

TABLE V

Pre Emergence Herbicidal Activity & Crop Tolerance

| | Compd. of Ex. 3 (Dosage in lb./acre) | | | Compd. of Ex. 4 (Dosage in lb./acre) | | | Compd. of Ex. 6 (Dosage in lb./acre) | | |
|---|---|---|---|---|---|---|---|---|---|
| PLANT | 4 | 2 | 1 | 4 | 2 | 1 | 4 | 2 | 1 |
| Morning Glory | $8^S$ | 3 | 2 | $5^S$ | $2^S$ | 0 | 4 | 5 | 3 |
| Mustard | 9 | $7^S$ | 3 | $8^{S+}$ | $7^S$ | 2 | 9 | $6^S$ | 2 |
| Yellow Foxtail | 9 | $7^S$ | 3 | $8^{S+}$ | $6^S$ | 2 | $8^{S+}$ | $7^S$ | 4 |
| Japanese Millet | $8^S$ | $6^S$ | 3 | $8^S$ | 4 | 2 | $8^S$ | $5^S$ | 3 |
| Crabgrass | 9 | 9 | $7^S$ | 9 | 9 | $4^{S+}$ | 9 | 9 | 9 |
| Pigweed | 9 | 9 | 9 | 9 | 9 | 9 | 9 | 9 | 9 |
| Cocklebur | 9 | 9 | $5^S$ | 9 | 9 | 5 | $8^{S+}$ | $8^{S+}$ | 9 |
| Velvet Leaf | 9 | $3^S$ | $5^S$ | 9 | 5 | 9 | $8^{S+}$ | $8^{S+}$ | $8^{S+}$ |
| Hemp Sesbania | 9 | $8^S$ | 9 | 9 | $8^S$ | $7^S$ | 9 | 9 | 9 |
| Lambsquarters | 9 | 9 | 9 | 9 | 9 | 9 | 9 | 9 | 9 |
| Cotton | $4^S$ | — | | | | | $3^S$ | | |
| Soybean | 3 | — | | | | | 3 | | |
| Corn | 0 | — | | | | | 4 | | |
| Wheat | 3 | — | | | | | $6^S$ | | |
| Rice | 4 | — | | | | | 2 | | |

In the above Tables IV and V, $S$ = stunting; $S+$ = severe stunting

EXAMPLE 9

Crop Selectivity

This example shows the crop selectivity of various types of the substituted m-phenoxybenzoates of this invention as compared to a commercial herbicide

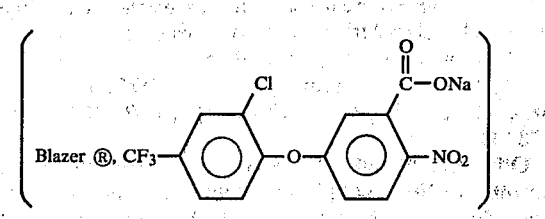

on a number of agronomic crops. Following the general test procedure of Examples 7 and 8, aqueous solutions of the various m-phenoxybenzoates are evaluated for significant tolerance towards important crops. The results of these tests are as reported in Table VI.

TABLE VI

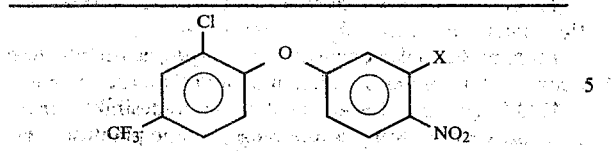

Selectivity in Post-Emergence Herbicidal Tests (at 2 lb./acre)

| Compound of Ex. | X | Plant Injury* Corn | Soybean | Rice |
|---|---|---|---|---|
| 3 | —COCH₂CH₂OC—C—CH₃ (with three C=O) | 1 | 3 | 3 |
| 4 | —COCH₂CH₂OC—C—C₂H₅ (with three C=O) | 2 | 3 | 1 |
| 5 | —COCH₂CH₂OCC₂H₄COCH₃ (with three C=O) | 1 | 2 | 0 |
| 6 | —COCH₂CH₂OS—N(CH₃)₂ (with C=O, S(=O)₂) | 0 | 4 | 2 |
| Comparative | —CONa | 9 | 4ˢ | 8ˢ⁺ |

Selectivity in Pre-Emergence Herbicidal Tests (at 2 lb./acre)

| Compound of Ex. | X | Plant Injury* Corn | Soybean | Rice |
|---|---|---|---|---|
| 3 | As Above | 0 | 3 | 4 |
| 5 | As Above | 0 | 9 | 1ˢ |
| 6 | As Above | 4 | 3 | 2 |
| Comparative | As Above | 5 | 9 | 7ˢ |

*Rated on scale of 0 to 9, from no visible effect on foliage to 100% destruction; with S = moderate stunting and S⁺ = severe stunting.

In summary, the compounds of this invention show high pre- and post-emergence herbicidal activity against indicator weeds, and are particularly effective against broadleaf weeds, such as morning glory. In addition to such effective herbicidal activity, they exhibit an unusual selectivity against important agronomic crops, such as corn, wheat, soybean and rice.

While the invention has been described with particular reference to certain embodiments thereof, it will be understood that certain modifications and changes may be made which are within the skill of the art. Therefore it is intended to be bound only by the appended claims.

What is claimed is:

1. A herbicidal compound having the formula

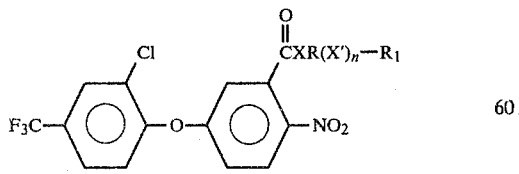

wherein

R is a saturated or unsaturated, straight chain or branched aliphatic hydrocarbon radical of from 1 to 18 carbon atoms wherein one or more of the —CH₂— groups can be replaced with —O—, —S—, —S—S—, —SO—, —SO₂— or —NR₂— and said hydrocarbon radical is optionally substituted with halogen, trihalomethyl, cyano, aryl, hydroxy, alkoxy, nitro or cycloalkyl having 3 to 6 carbon atoms;

$R_1$ is

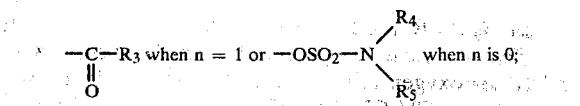

$R_3$ is

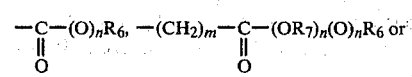

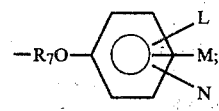

$R_2$ is hydrogen or a saturated or unsaturated straight or branched chain aliphatic radical having from 1 to 8 carbon atoms, optionally substituted with halogen, hydroxy, alkoxy, cyano or nitro;

$R_4$ and $R_5$ are independently a saturated or unsaturated, straight or branched chain aliphatic radical having 1 to 8 carbon atoms optionally substituted with halogen, trihalomethyl, alkoxy or cyano; hydrogen or phenyl optionally substituted with halogen, alkyl, alkoxy, trihalomethyl, nitro or cyano;

$R_6$ is a saturated or unsaturated straight chain or branched aliphatic radical containing from 1 to 8 carbon atoms, optionally substituted with halogen, trihalomethyl, cyano, hydroxy, nitro, acetoxy, alkoxy, thioalkoxy or aryl; an aryl radical optionally substituted with halogen, trihalomethyl, hydroxy, cyano, nitro, alkyl or alkoxy; a cyclic 3–6 membered ring alkylene or 5–6 membered ring alkenylene or benzyl optionally substituted with halogen, trihalomethyl, alkyl, hydroxy, alkoxy or cyano;

$R_7$ is an alkylene diradical having from 1 to 6 carbon atoms;

X and X' are each independently —O—, —S— or —NR₂—

L, M and N are each independently hydrogen, hydroxy, halogen, trihalomethyl, nitro, cyano, alkyl or alkoxy having from 1 to 4 carbon atoms and

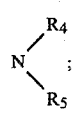

m has a value of from 1 to 6 and n in each instance has a value of from 0 to 1.

2. The herbicidal compound of claim 1 having the formula

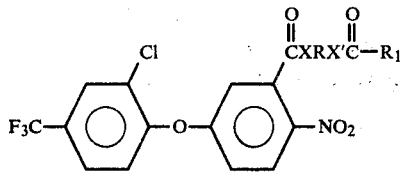

wherein X, X', R and R' are as defined in claim 1.

3. The herbicidal compound of claim 2 wherein X and X' are oxygen atoms and R is a lower alkylene diradical or —(CH$_2$CH$_2$O)$_p$—CH$_2$CH$_2$— where p has a value of from 1 to 8.

4. The herbicidal compound of claim 2 wherein X and X' are —NR$_2$— and R$_2$ is hydrogen or lower alkyl.

5. The herbicidal compound of claim 1 which is 2-(methyloxalyloxy) ethyl 5-(2-chloro-4-trifluoromethylphenoxy)-2-nitrobenzoate.

6. The herbicidal compound of claim 1 which is 2-2-(methoxycarbonyl) propionyloxy ethyl 5-(2-chloro-4-trifluoromethylphenoxy)-2-nitrobenzoate.

7. The herbicidal compound of claim 1 which is 2-(ethyloxalyloxy) ethyl 5-(2-chloro-4-trifluoromethylphenoxy)-2-nitrobenzoate.

8. The herbicidal compound of claim 1 which is 2-(2,4-dichlorophenoxyacetoxy)ethyl 5-(2-chloro-4-trifluoromethylphenoxy)-2-nitrobenzoate.

9. The herbicidal compound of claim 1 which is 8-(2,4-dichlorophenoxyacetoxy)-3,6-dioxaoctyl 5-(2-chloro-4-trifluoromethylphenoxy)-2-nitrobenzoate.

10. The herbicidal compound of claim 1 having the formula

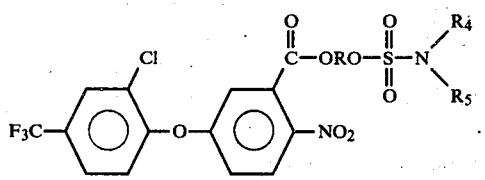

wherein R is an aliphatic diradical having 1 to 6 carbon atoms selected from the group of alkylene diradical or an alkylene diradical interrupted by an oxygen atom and R$_4$ and R$_5$ are each independently lower alkyl, phenyl or halogenated phenyl.

11. The herbicidal compound of claim 10 which is 2-(N,N-dimethylsulfamoyloxy)ethyl 5-(2-chloro-4-trifluoromethylphenoxy)-2-nitrobenzoate.

12. A herbicidal composition comprising an effective amount of a compound of claim 1 and an inert carrier.

13. A process for controlling undesirable plant growth which comprises applying to the plant or plant situs a growth controlling amount of the herbicidal compound of claim 1.

14. The process of claim 13 wherein the herbicidal compound is applied at a rate of between about 0.05 and about 8 pounds per acre.

15. The process of claim 13 wherein the herbicidal compound is applied in combination with an inert carrier as a liquid spray.

16. The process of claim 13 wherein herbicidal compound is applied in combination with an inert solid carrier as a dust or granulated mixture.

17. The process of claim 13 wherein the compound of claim 1 is applied as a post emergent treatment.

18. The process of claim 13 wherein the compound of claim 1 is applied as a pre emergent treatment.

19. The herbicidal compound of claim 1 where X and X' are oxygen; n is 1; R is an ethylene radical and R$_1$ is

20. The herbicidal compound of claim 19 where R$_3$ is

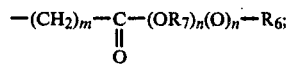

m is 2 and n is 0.

21. The herbicidal compound of claim 20 having the formula

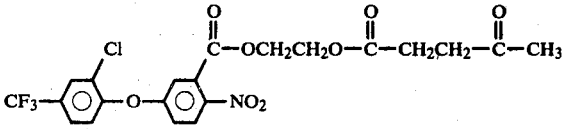

* * * * *